United States Patent [19]

Fourcin et al.

[11] Patent Number: 4,510,936
[45] Date of Patent: Apr. 16, 1985

[54] APPARATUS FOR THE ELECTRICAL STIMULATION OF NERVES

[75] Inventors: Adrian J. Fourcin; David M. Howard, both of London; John R. Walliker, Epsom, all of England

[73] Assignee: National Research Development Corporation, London, England

[21] Appl. No.: 572,402

[22] Filed: Jan. 20, 1984

[30] Foreign Application Priority Data

Jan. 20, 1983 [GB] United Kingdom ............... 8301526

[51] Int. Cl.³ ............................................. A61N 1/36
[52] U.S. Cl. ............................... 128/419 R; 128/1 R
[58] Field of Search .................... 128/419 R, 1 R; 179/107 R, 107 BC

[56] References Cited

U.S. PATENT DOCUMENTS

| 3,841,305 | 10/1974 | Hallgren | 128/419 R X |
| 4,419,995 | 12/1983 | Hochmain et al. | 128/419 R |
| 4,428,377 | 1/1984 | Zollner et al. | 128/419 R |

FOREIGN PATENT DOCUMENTS

| 54418 | 6/1982 | European Pat. Off. | 128/419 R |
| 2811120 | 9/1978 | Fed. Rep. of Germany | 128/419 R |
| WO83/01006 | 3/1983 | PCT Int'l Appl. | 128/419 R |

OTHER PUBLICATIONS

Rosen et al., "Voice Pitch as an Aid to Lip Reading" *Nature*, vol. 291, 5-14-81, pp. 150-152.
Gruenz et al., "Extraction and Portrayal of Pitch of Speech Sounds", Jrnl. Acoustical Soc. of Am., 1949, pp. 487-495.
Fourcin et al., "Speech Perception with Promontory Stimulation", New York Acad. of Science, 4/14-16/82.
Forster, "Theoretical Design . . . Neural Prosthesis Applications", J. Biomed. Eng., vol. 3, Apr., 1981, pp. 107-120.
Gheewala et al., "CMOS . . . Stimulator for the Deaf" IEEE Jrnl. of Solid State Cir., vol. SC-10, No. 6, pp. 472-479, Dec. 1975.
Dillier et al., "Computer Controlled Test System . . . ", Scand. Audiol. Suppl. II, 1980, pp. 163-170.

*Primary Examiner*—Edward M. Coven
*Attorney, Agent, or Firm*—Cushman, Darby & Cushman

[57] ABSTRACT

Apparatus primarily for stimulating the auditory nerve in the vicinity of the cochlea of deaf persons to give a sensation indicative of the pitch of speech is described. The stimulus which is in the form of an alternating current of varying period dependent on the pitch of speech is applied to an electrode positioned in the vicinity of the cochlea. The current is non-zero for most of the duration of most stimulation periods and in order to elicit a stable auditory sensation d.c. baseline fluctuation is prevented by the use of a controlled current generator. The period of speech sounds is found using a specially devised circuit and a voltage related to the frequency of such sounds is determined by a period-to-voltage converter and a reciprocal circuit, this voltage being supplied as a control signal for the current generator. An alternative microcomputer version is also described. In order to give an indication of the presence of voiceless sounds, a detector capable of distinguishing between voiced and voiceless sounds is also included together with a noise source which is coupled to the stimulation electrode when the detector indicates the presence of voiceless sounds.

17 Claims, 14 Drawing Figures

APPARATUS FOR THE ELECTRICAL STIMULATION OF NERVES

The present invention is related to the application of an electrical stimulus to nerves, particularly the nerves of the cochlea, and to the generation of a suitable stimulus both for voiced and voiceless sounds. Many patients who have total loss of hearing can be given a sensation of hearing by applying an electrical stimulus to the cochlea. The sensation is frequency dependent in the sense that the patient can distinguish for example between different larynx frequencies.

Such stimulation is useful to the totally deaf lipreader since the appreciation of different frequencies resolves many of the speech contrastive ambiguities which are otherwise encountered.

Suitable electrodes for applying a stimulus to the cochlea are, for example, based on the use of a conventional ear mould providing a mechanical base for a ball-ended electrode assembly. The ear mould is gold coated on its external meatal surface to provide an electrical return path and the assembly itself comprises a ball-ended axially sprung stem which is adjusted for each individual patient. In order to use such an electrode patients must have either an open middle ear as a result of, for example, the treatment of mastoiditis or a closed auditory meatus in which the tympanic membrane has been sectioned and displaced by a tympanopexy operation so that it is in intimate contact with the promontory. The ball-ended electrode makes direct contact with the promontory of the open-ear patient and for a closed ear patient contact is made to the cochlea via the tympanic membrane.

Internal conducting paths may be implanted so as to facilitate the passage of stimulating current to the round window or more directly to the inner ear.

According to a first aspect of the present invention there is provided apparatus for the electrical stimulation of nerves comprising stimulus means for generating an electrical stimulus of alternating polarity and varying periods, which is non-zero for most of the duration of most of the said periods, an electrode for location in a position where a nerve can be stimulated, and charge control means for ensuring that the net charge applied to the electrode is zero in each of successive intervals substantially throughout stimulation, each interval having a duration equal to an integral number of said periods not greater than three.

The patient is protected by the invention since any small residual d.c. component applied to the electrode is unlikely to result in electrochemical or other damage. In addition, as a safety feature, the apparatus preferably includes a capacitor coupled between the stimulus means and the electrode, the charge control means, in operation, ensuring that the net charge applied to the capacitor is zero in each of said successive intervals.

The introduction of the capacitor would ordinarily result in a floating d.c. baseline at the stimulus electrodes, and in order to elicit a stable auditory sensation in the patient, d.c. baseline fluctuation must be prevented. The charge-control means overcomes this problem by ensuring that the mean output current from the capacitor is zero.

Intra cochlear methods of stimulating the auditory nerve by employing biphasic pulses of short duration relative to the stimulation period are known. However, when this type of stimulation is used external to the cochlea other nerves may be stimulated so that, for example, a facial twitch may occur. For extracochlear stimulation the inventors have found that a stimulus with low frequency spectral weighting is best, that is a stimulus of the type mentioned above which is non-zero for most of the duration of each period of stimulation.

Thus it is a feature of the present invention that the stimulus be applied at a low frequency and with long pulse widths. In the case of stimulation of the cochlea, the stimulation frequency should be equal to or below the frequency corresponding to the "pitch" period of voiced sounds originating the stimulation waveform.

In voiced sounds it is difficult to determine a true fundamental period from frequency analysis because although waveforms are similar for a number of periods there are differences from one period to the next and when changes occur, they may do so suddenly. In this specification the period of a voiced sound (voice period) is defined as the interval between successive sound pressure maxima which occur when the vocal folds of the larynx are closed. This period is also often referred to as the "pitch" period.

Preferably apparatus according to the invention includes means for determining the voice period, and the means for generating an electrical stimulus are constructed to generate one alternating current cycle per voice period, the net charge supplied to the capacitor being zero in this voice period. The means for determining voice period may generate one pulse each time one of the said maxima occurs.

According to a second aspect of the invention there is provided apparatus for determining the voice period of voiced sounds comprising a transducer for providing an electrical signal representative of sounds, a logarithmic amplifier coupled to the transducer by way of a low-pass filter, and peak detection means coupled to the amplifier output and arranged to respond to the first peak in each voice period of the sound representative signal to generate an output pulse each time the said signal indicates that the vocal cords of a speaker making the voiced sounds have closed.

Since stimulation on this basis cannot usually proceed until a complete voice period has occurred the apparatus may include means for discarding said pulses unless a preceding pulse occurred within an interval which is not longer than the longest expected pitch period. In this way no periodic stimulus will be generated after silence or a voiceless sound until one complete pitch period has been received and the appropriate waveform to produce net zero charge at the stimulating electrode can be applied to the capacitor.

Although it is an advantage to stimulate the patient synchronously with the speaker's lip movements a delay of up to 30 mS will not substantially impair lip reading. The analysis techniques described above can in consequence be associated with a running store of up to this length so that additional signal processing algorithms may be applied.

The apparatus may also include means for ending stimulation when the last pitch period in a voiced sound has been received. Such means may allow the generation of one cycle of the stimulation waveform only each time a pitch period is detected so that when pitch periods are no longer detected stimulation ceases.

The apparatus or means for determining the voice period may comprise an appropriately phased microphone coupled by way of a low-pass filter and a logarithmic amplifier to peak detection means which generate one of the said pulses each time the sound received indicates that the vocal folds have closed. Preferably the microphone produces a phase distortion which is within a limit characterised as follows: the relative phase delay between the fundamental component and its second harmonic should not exceed 1/20 of the fundamental period. This gives, for example, a maximum delay of 714 microseconds for a fundamental frequency of 70 Hz at the lower end of a typical adult male's frequency range. By using a low phase distortion microphone the first positive pressure waveform peak in each voice period is not slurred by phase distortion and can be more easily detected by the peak detector means. The use of a logarithmic amplifier reduces the dynamic range of the input signal from the microphone.

The upper end frequency range to which the cochlea is sensitive to electrical stimulation may be just below frequencies corresponding to the voice periods generated at the upper end of the frequency range of a man's speech and appreciably less than the upper end of the frequency ranges of voice periods of women and children. In order to overcome this problem the apparatus may include means for reducing the frequency of the stimulus from the frequency which corresponds to voice period and the net charge transmitted via the isolating capacitor is then zero preferably in each period corresponding to the reduced frequency. Reduction can be on a linear basis but some other basis may be used. For example a reduction corresponding to simple frequency subtraction has the advantages of augmenting proportional changes at the lower end of the frequency range, and period mapping can give uniform enhancement of proportional changes in stimulating frequency.

Since voiceless sounds are also useful in resolving ambiguities for lip-readers, the apparatus preferably includes means for providing a distinctive stimulus when voiceless sounds occur. The said means may be responsive to the lengths of periods between zero crossings in a speech signal measured in succession. Such means may be used independently of the apparatus according to the first aspect of the invention.

According to a third aspect of the present invention there is provided apparatus for distinguishing between voiced and voiceless speech sounds comprising means suitable for coupling to a sound transducer for determining respective intervals between signal reversals in the transducer output signal, means for indicating the presence of voiceless sounds when, in each of a group of pairs of successive said intervals, the durations of the intervals are both shorter than a predetermined interval.

Apparatus according to the third aspect of the invention preferably includes means for indicating the presence of voiced sounds when, in each of a group of pairs of successive said intervals, the duration of the first interval is in a first predetermined range and the duration of the second interval is in a second predetermined range.

The predetermined interval and predetermined ranges depend on preprocessing (if any) carried out before signals reach the means for determining respective intervals, and can be found experimentally. One example of each is given below and relates to specified preprocessing also exemplified.

Methods corresponding to the three aspects of the invention and the variations mentioned in the specification also form part of the invention.

Certain embodiments of the invention will now be described by way of example, with reference to the accompanying drawings, in which.

A basic requirement of the present invention is the derivation of a signal representing the voice period of voiced sounds. Each voice period commences with a peak corresponding to the closure of the vocal folds in the larynx and as is mentioned above the voice period is the interval between these first peaks.

Figure 1:
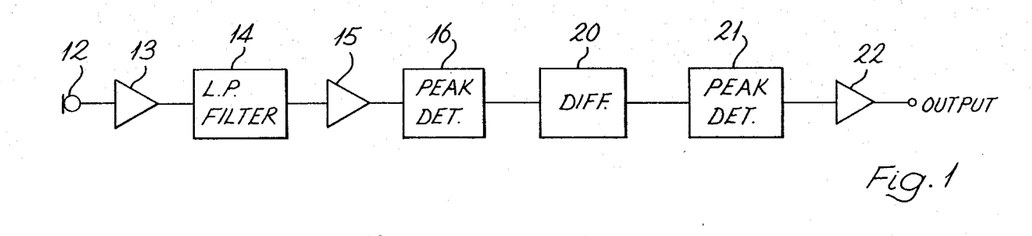
FIG. 1 is a block diagram of a voice period extractor used in an embodiment of the invention.

The voice period is required in order to achieve charge balancing by ensuring that a capacitor coupling the circuits driving the stimulating electrode to the electrode receives zero charge over an interval, in the embodiment of FIG. 1, of one voice period. The voice period is also required because the frequency of oscillations passed to the electrode is determined by the voice period.

A circuit for determining voice period is shown in FIG. 1 and comprises a microphone 12 having low phase distortion in the frequency range 50 to 500 Hz coupled by way of an amplifier 13 to a two-stage four-pole low-pass Butterworth filter 14 having a cut-off frequency of 450 Hz. The purpose of this filter is to remove high frequencies which are not relevant to the voice period. The microphone is so phased (that is connected) that positive going pressure input (that is a pressure increase) produces a positive going voltage waveform at a terminal 24 (see FIG. 3) in a peak detector circuit 16.

Figure 2A:
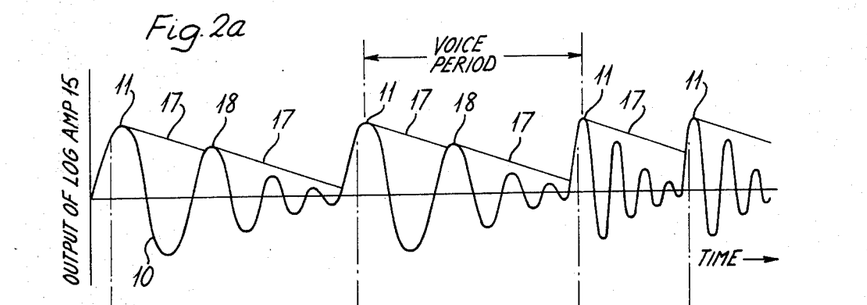
FIGS. 2a to 2d show waveforms used in explaining the operation of the circuits shown in the figures.
Figure 2B:
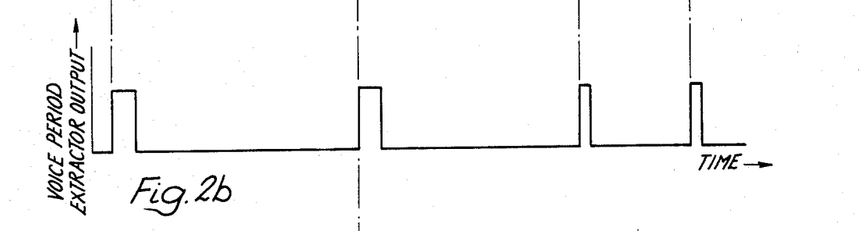

In view of the large dynamic range of input signals at the microphone 12 the output from the low pass filter 14 is passed to a logarithmic amplifier 15 having an output always within a suitable magnitude range for application to the first peak detection circuit 16. A convenient simplified illustration of the waveform at the output of the logarithmic amplifier 15 is shown at 10 in FIG. 2a, and a voice period is shown between two peaks 11 corresponding to first positive pressure peaks in two successive periods. Peaks are detected by using a capacitor which charges from the output of the amplifier 15 with a low time constant and discharges linearly at a relatively high time constant. The latter is chosen to prevent peaks following the initial peak in each peak period of the waveform 10 from causing the capacitor to recharge. Since this choice cannot be made satisfactorily to cover the complete range of expected pitch periods a compromise lower time constant is chosen which in some circumstances allows the second peak in each pitch period to start to charge the capacitor again. This situation is shown in FIG. 1a where the discharge of the capacitor is represented by the line 17. In the last two pitch periods the second peak is insufficient to recharge the capacitor whereas in the first two pitch periods recharging occurs at second peaks 18. Thus the output from the first peak detector circuit 16 is generally "sawtooth" in nature but may contain minor peaks at points 18. By passing this waveform through a differentiation circuit 20 the leading edges of each "sawtooth" where rate of change is high are enhanced with respect to any minor peaks. The differentiated signals are passed to a second peak detection circuit 21 which operates in the same way as the peak detection circuit 16 and may conveniently have the same time constants. A comparator 22 is used to provide an output when the signal from the peak detection circuit 21 is above a threshold level and in this way a pulse waveform of the type shown in FIG. 2b is generated, one relatively short duration pulse being generated for each pitch period in the waveform from the microphone 12.

Figure 3:
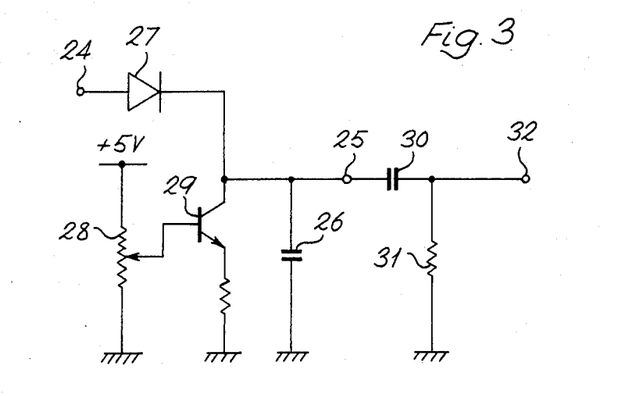
FIG. 3 is a circuit diagram of a peak detector circuit and differentiator used in the apparatus of FIG. 2.

A suitable circuit for the peak detector circuits 16 and 21 is shown between terminals 24 and 25 in FIG. 3. The capacitor 26 is charged by way of a signal diode 27 whenever the input signal at the terminal 24 is greater than the voltage across the capacitor 26. A transistor 29 continually discharges the capacitor 26 at a constant but adjustable rate set by a potentiometer 28. It is important to ensure that the diode 27 is poled as shown so that the first positive acoustic pressure peak generated in each pitch period causes the diode to conduct. Since the capacitor 26 is discharged at a constant rate the discharge indicated by the line 17 in FIG. 2a is linear not exponential and this is an advantage in distinguising between the first peak in each pitch period and subsequent peaks as can be seen from FIG. 2a where the line 17 is higher than it would be for exponential discharge.

A simple differentiator circuit comprising a capacitor 30 and a resistor 31 is shown between the terminal 25 and a terminal 32. This circuit corresponds to the circuit 20 of FIG. 1.

Figure 4:
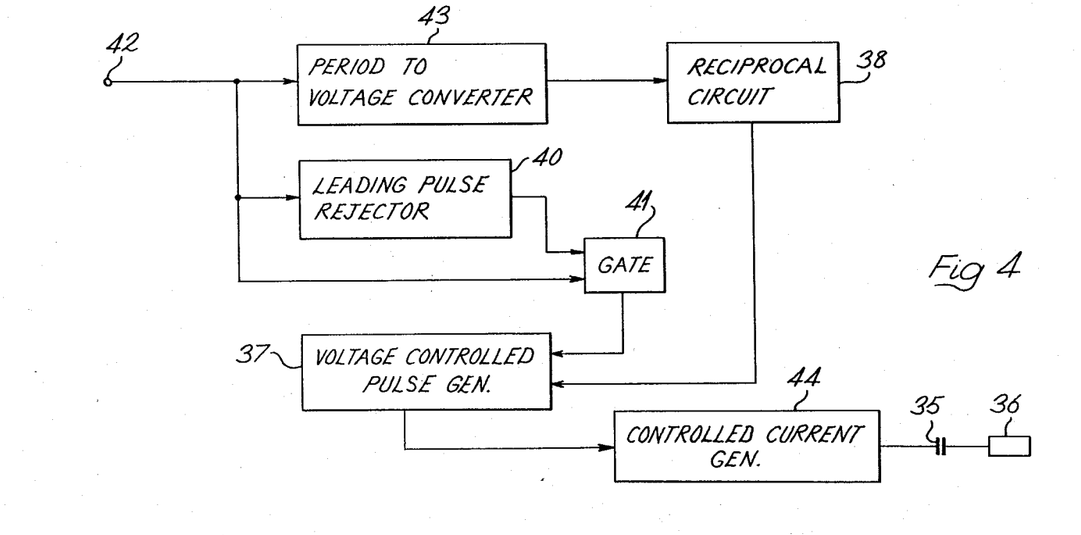
FIG. 4 is a block diagram of apparatus according to the invention.

Using the arrangement shown in FIG. 4 the net charge supplied to the capacitor 35 which isolates a stimulation electrode 36 positioned within a patient's ear on the cochlea promontory is zero for each pitch period. This is achieved by means of a voltage controlled rectangular pulse generator 37 which receives a signal controlling the frequency of oscillation from a reciprocal circuit 38 whose output represents the frequency corresponding to each pitch period. Since a pitch period cannot be determined until the second of the pulses of the type shown in FIG. 2b is received, a rejection circuit 40 which rejects leading pulses and a gate 41 enable the rectangular pulse generator 37 only when two pitch-period pulses have been received at a terminal 42. Such pulses may be supplied from the circuit of FIG. 1 by a direct connection or, for example, an infra-red link (not shown) where it is required to keep the patient's apparatus as small as possible by having the circuits of FIG. 1 separately installed. The gate 41 has a further function: when a period of silence follows a voiced sound it is necessary to cease stimulation as soon as possible and not continue at the last generated frequency. This is achieved by allowing stimulation to continue for one pitch period only. A period-to-voltage converter circuit 43 supplies a voltage representative of each pitch period to the circuit 38, and a controlled current output generator 44 having gain control is connected between the pulse generator 37 and the capacitor 35.

Figure 5:
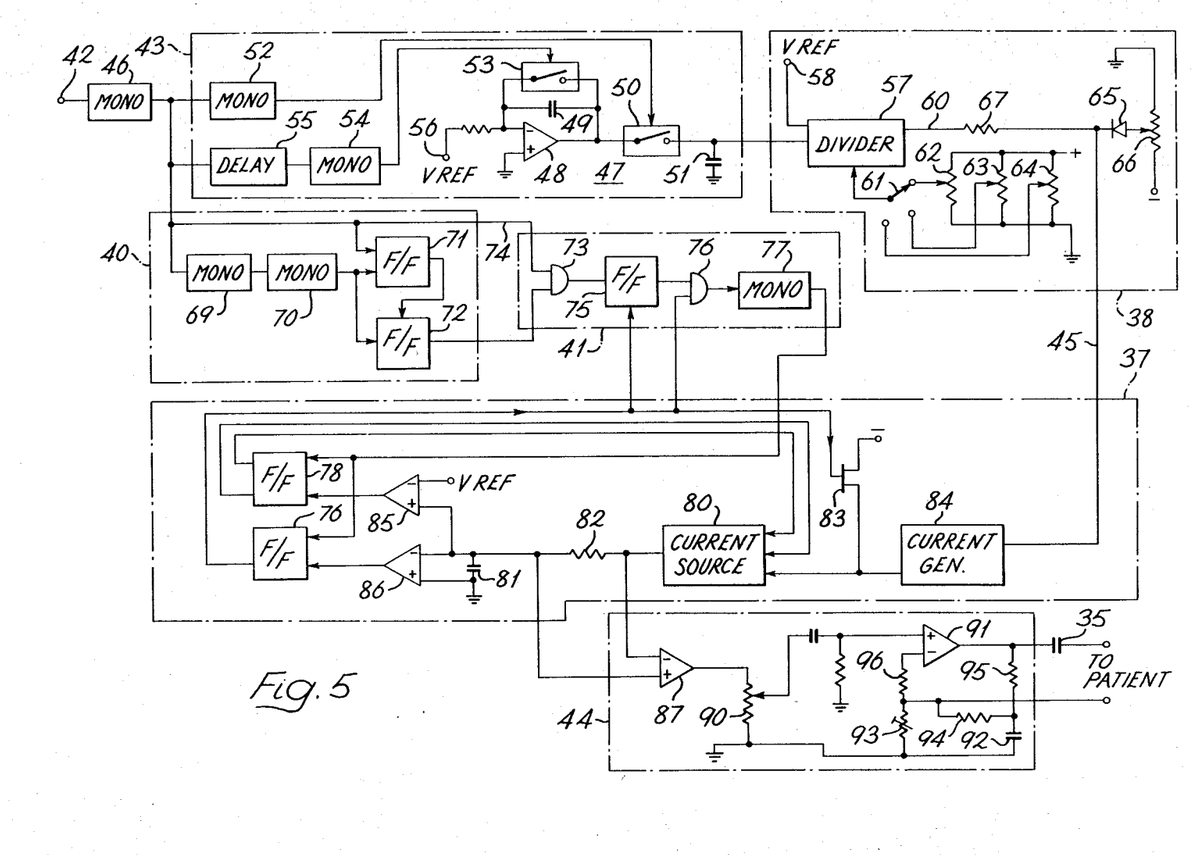
FIG. 5 shows the circuit of FIG. 4 in more detail.

In FIG. 5 the circuits shown in FIG. 4 are indicated by dashed lines. The repetition frequency of the stimulus applied to the patient is controlled by the voltage on a line 45 which is derived as follows. The pulses indicating pitch periods are applied to a monostable circuit 46 from the terminal 42, this monostable circuit generating fixed duration pulses of one millisecond each. The one millisecond pulses control an integrator 47 formed by an operational amplifier 48 and a shunt capacitor 49. When each pulse from the monostable 46 is received the output of the integrator 47 is transferred by a switch 50 to a storage capacitor 51. The switch 50 may be a CMOS transmission gate and is controlled by a pulse generated by a monostable circuit 52 immediately a pulse is received from the monostable 46. Having achieved transfer of the integrator output the integrator is reset to zero by means of a switch 53 operated by a monostable circuit 54 after a delay introduced by delay circuit 55.

The voltage stored on the capacitor 51 depends on the interval between pulses from the monostable 46 because the integrator 47 charges from a constant reference voltage applied at a terminal 56. The voltage stored is therefore proportional to each pitch period as it occurs and in order to form the reciprocal of the pitch period the stored voltage is applied to an integrated divider circuit 57 (type BB 4214). A reference voltage applied to a terminal 58 forms the numerator from which a quotient representative of the required reciprocal is derived. A voltage proportional to the quotient appears on an output line 60 after modification by means of a voltage applied by way of a switch 61.

As has already been explained it is useful in many cases to translate the frequency corresponding to pitch period to a lower frequency which is in a range where a patient responds better to stimulation. In FIG. 5 this translation of frequency is achieved by deducting a voltage selected by means of the switch 61 from three potentiometers 62, 63 and 64 since it is a property of the integrated circuit mentioned above that the output voltage is reduced by an amount proportional to a voltage applied at a terminal and it is this terminal which is connected to the switch 61. The voltage applied by the switch 61 need not be reduced by a fixed amount for all frequencies and it may be advantageous to apply a voltage which is a function of voice period so that, for example, a constant enhancement of proportional changes is obtained.

As the stimulation frequency increases it is necessary to increase the magnitude of current supplied to the stimulation electrode. Otherwise the current applied in a short period is insufficient for stimulation. As will be described this increase is automatically made as frequency increases. The current cannot, however, be increased to the maximum the apparatus can provide since it becomes painful to the patient over a certain magnitude and for this reason an upper limit to the output voltage of the divider 57 is applied by means of a diode 65 and a potentiometer 66. Thus the required voltage on the line 45 appears between a resistor 67 and the diode 65, the resistor 67 having the function of increasing the output impedance from the divider 57 to a suitable value in relation to the potentiometer 66.

In order to carry out the functions of the pulse rejection circuit 40 and the gate 41 (cessation of stimulation when silence occurs) the pulses from the monostable 46 are applied to a monostable circuit 69 which generates pulses having a duration of 20 milliseconds, this being the longest pitch period expected. When pulses are received at intervals of less than 20 milliseconds a flip-flop circuit 71 is set by the first pulse from the monostable circuit 46 and the second such pulse resets the circuit 71 setting a flip-flop circuit 72 which then remains set enabling an AND gate 73. If a second pulse is not received from the circuit 46 within 20 milliseconds a monostable circuit 70 generates a one microsecond pulse which resets both circuits 71 and 72 closing the gate 73. Thus if a first pulse is received but no further pulse is received within 20 milliseconds then the first pulse is rejected as not being the first pulse in a new period of voiced sound. When the second and subsequent pulses within 20 milliseconds are applied to the AND gate 73 a flip-flop 75 is set whose function is to allow stimulation for one pitch period only at a time.

A monostable circuit 77 connected to the circuit 75 by way of an AND gate 76, enabled as explained below, then applies a pulse to flip-flop circuits 76 and 78 setting the former to a state in which it turns off a field effect transistor 83 allowing a control current from a current generator 84 to reach a bipolar current source 80 which may conveniently be type MJ 335. As a result current flows from the source 80 to a capacitor 81 by way of a resistor 82 and the direction of this current is determined by the state of the flip-flop 78. The magnitude of the current from the current generator 84 determines the magnitude of the current passed by the integrated circuit 80 to the capacitor 81.

Assuming that the capacitor 81 is not initially charged, it now charges until a comparator 85 indicates that it has reached a predetermined maximum voltage. At this maximum voltage the flip-flop circuit 78 changes to its other state and causes the integrated circuit 80 to discharge the capacitor 81 at the same rate (as governed by the current generator 84) and discharge continues until a comparator 86 signals that the voltage on the capacitor 81 has returned to zero. Thus the net charge on the capacitor 81 during the period of charge and discharge is zero. At this time the flip-flop 76 changes state, causing the field effect transistor 83 to conduct so that no current from the generator 84 reaches the integrated circuit 80 and current to the capacitor 81 ceases.

The higher the voltage applied on the line 45 the more current is supplied by the generator 84 to the integrated circuit 80 during the cycle of operations just described and the more quickly the capacitor 81 charges and discharges. In this way the frequency of stimulation is controlled by the voltage on the line 45. Also the requirement for increase in current with frequency is met.

The flip-flop circuit 75 is reset as soon as the flip-flop circuit 76 is set by a pulse from the monostable circuit 77, indicating that a cycle of stimulation has been initiated. However the AND gate 76 is only enabled by the circuit 76 at the end of a stimulation cycle. Thus if a new pulse from the monostable circuit 46 is received before the end of such a cycle as occurs during a rising frequency of stimulation the flip-flop circuit 75 is set to await a signal enabling the gate 76, when a new cycle is initiated immediately. Each voice period which is less than 20 milliseconds in duration therefore causes one cycle of stimulation to be generated, periods of longer duration being rejected by the circuits 69 to 72.

The voltage across the resistor 82 is applied to a differential amplifier 87 so that the voltage applied to a potentiometer 90 is constant while constant current flows in the resistor 82 but this voltage depends upon the voltage across the resistor 82 and reverses when the current in the resistor 82 changes from charging to discharging the capacitor 81. The potentiometer 90 is a volume control for the patient and its output is applied by way of an operational amplifier 91 and the capacitor 35 to stimulate the patient's cochlea. Thus stimulation is generated for the whole of each voice period except very briefly when current in the resistor 82 changes direction. In the absence of a capacitor 92 and resistors 94 and 95 the voltage applied to the capacitor 35 would drift to the maximum of the supply rail but the feedback resistors 94 and 95 stabilise the circuit at very low frequencies and d.c. while the capacitor 92 prevents these resistors from influencing the operation of the circuit at the higher stimulating frequencies. A resistor 96 limits the peak current flowing to the stimulating electrode in the event of a failure in the amplifier 91.

Since the charge delivered by the amplifier 91 to the capacitor 35 depends on the current through the resistor 82 and the charge passed through this resistor is zero in each pitch period, the net charge passed via the capacitor 35 to the electrodes is also zero in each such period.

Figure 2C:
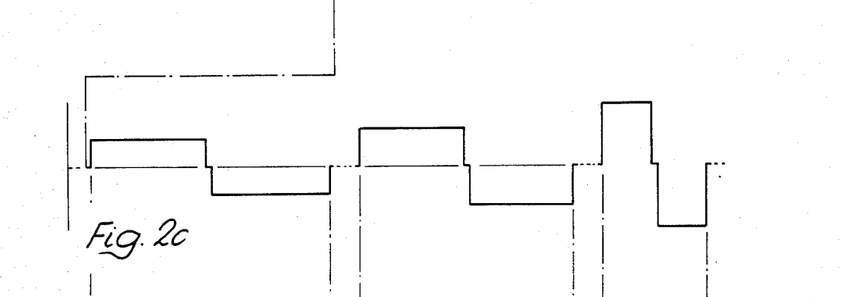

FIG. 2c shows the output pulses generated at the potentiometer 90 by the circuit of FIG. 5. Since the first pair of pulses appear after the end of the voice period to which they relate the time axis of FIG. 2c is broken and the dashed line from FIG. 2b indicates corresponding times.

Figure 8:
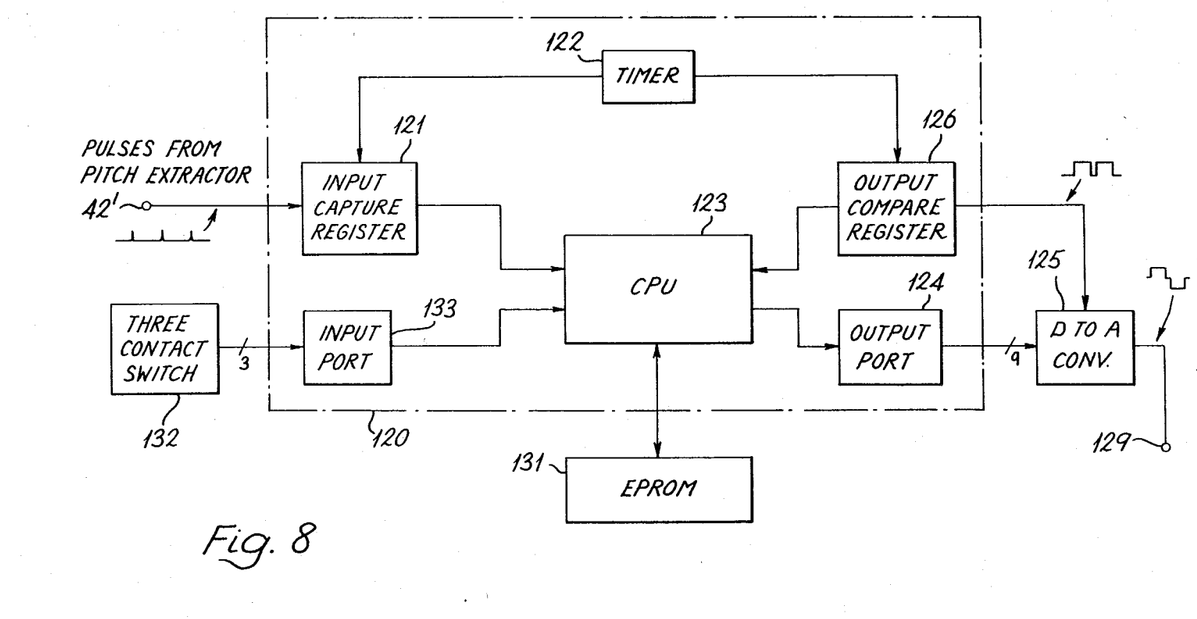
FIG. 8 shows a microcomputer alternative for some of the circuits of FIG. 4, and FIGS. 9 to 11 are flow diagrams used in explaining the operation of FIG. 8.

An alternative to the circuits 37, 38, 40, 41 and 43 of FIGS. 4 and 5 is now described. In FIG. 8 an input terminal 42' of a single chip microcomputer unit 120 receives signals from the voice period extractor circuit of FIG. 1. When a pulse is received at the terminal 42', an input capture register 121 is loaded with the current value of a free running 16-bit 1 MHz timer 122. As is explained below this procedure allows the duration of voice periods to be measured by a central processing unit (CPU) 123 which provides a digital output at a port 124 (typically 9-bit). The digital output is converted to an analogue rectangular waveform appearing at a terminal 129 by a multiplying digital-to-analogue converter 125 which includes an operational amplifier (now shown). The timing of this waveform is under the control of an output compare register 126 which provides gating pulses when the count in the timer reaches a value set in the register 126 by the CPU 123. After reaching the terminal 129 which is connected to the upper end of the potentiometer 90 (the patient's gain control) in a circuit 44 similar to that shown in FIG. 5, the rectangular waveform passes to a capacitor 35 and the output electrode.

The program for the microcomputer 120 is held in an erasable programmable read-only memory (EPROM) 131 connected to the CPU 123. A three contact switch 132 is connected by a three wire (and common wire) connection to an input port 133 and thence to the CPU 123. The function of the switch 132 is to control the selection of waveform amplitude and frequency in response to various voice periods since as mentioned above there is often a need to lengthen period before application to the patient's electrode. An increase in waveform amplitude with increase in frequency is often also useful. The EPROM 131 also contains look-up tables containing periods and amplitudes for use by the CPU 123 under selection control by the switch 132, and these tables can be tailored to individual patients by measurement and "trial and error".

An Hitachi HD 63 PO1M1 microcomputer system may be used as the unit 120, and this unit type has provision for a "piggy back" EPROM which may be of type NMC 27C32-45 made by National Semi-conductor. The types of microcomputer unit and EPROM mentioned are constructed using CMOS technology which results in low power consumption. A SLEEP instruction is available which shuts down the CPU and the EPROM while leaving peripheral devices active, so reducing power consumption further.

When the circuit of FIG. 8 is constructed using components of the above mentioned type, or with similar properties, and the CPU is appropriately programmed, initialisation of input/output ports, status flags and memory variables occurs when power is switched on. At the same time the timer 122 starts, but the CPU and EPROM are programmed to wait in sleep mode until an interrupt occurs, and on return from interrupt the sleep mode is again entered unless another interrupt has meanwhile occurred and is awaiting service.

Figure 9:
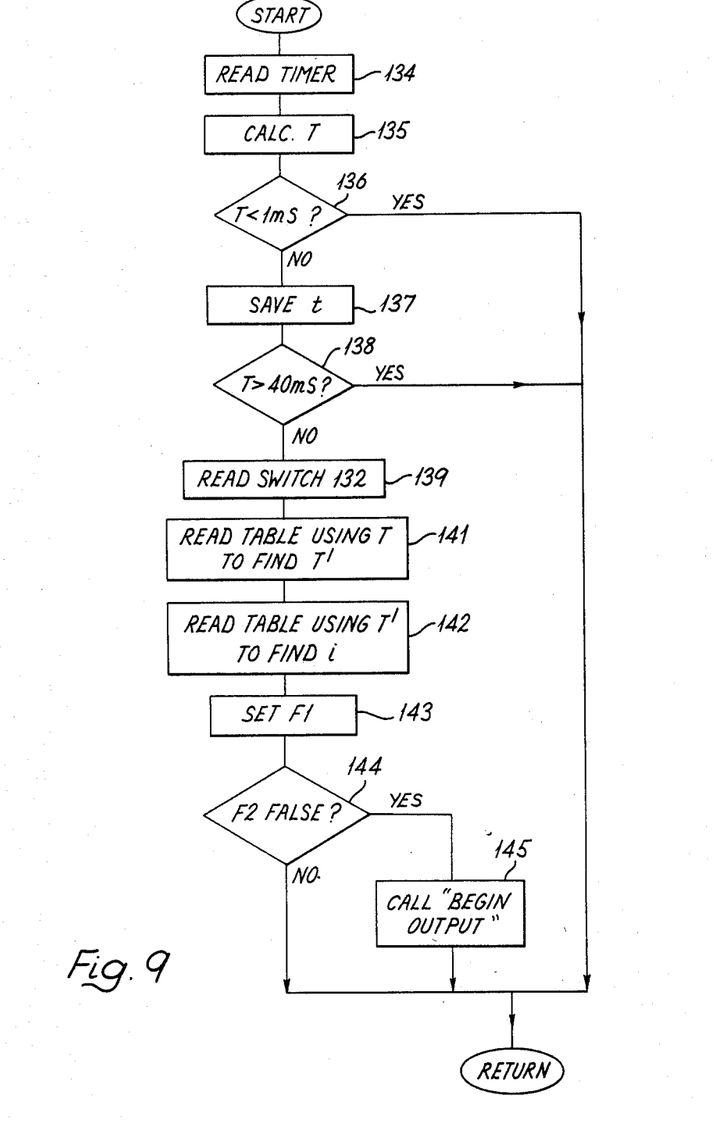

When a pulse from the voice pitch extractor is received at the terminal 42' an "input capture" interrupt routine shown in FIG. 9 is initiated. The terminal 122 is read in an operation 134 and then a variable T is calculated from the time of occurrence of the previous pulse from the pitch extractor (operation 135). A test 136 is carried out to determine whether T is less than for example 1 mS (which is the shortest expected voice period) and if so the last detector pulse is considered to be spurious and a return from the routine occurs. If T is greater than, for example 1 mS the time t of the current detector pulse is saved (operation 137). A test 138 is then carried out to determine whether T is greater than, for example 40 mS and if so the period up to the reception of the last extractor pulse is considered to be silent and a return from the subroutine occurs. If the test 138 is negative the switch 132 is read (operation 139) and then an appropriate variable T' representing the period of the stimulation pulse applied to the electrode is found using one of the previously mentioned look-up tables held by the EPROM 131 (unless the switch 132 indicates that the period T' is to be set to T). Having found T' another of the previously mentioned look-up tables is used to find the amplitude (i) of the squarewave current to be applied to the electrode (operation 142). A "data available flag" F1 is then set in an operation 143 and a test 144 is made to discover whether an "output in progress" flag F2 is false. If so then the "begin output" routine is called in an operation 145 and when the subroutine is completed a return follows. If the flag F2 is true then an immediate return occurs.

Figure 10:
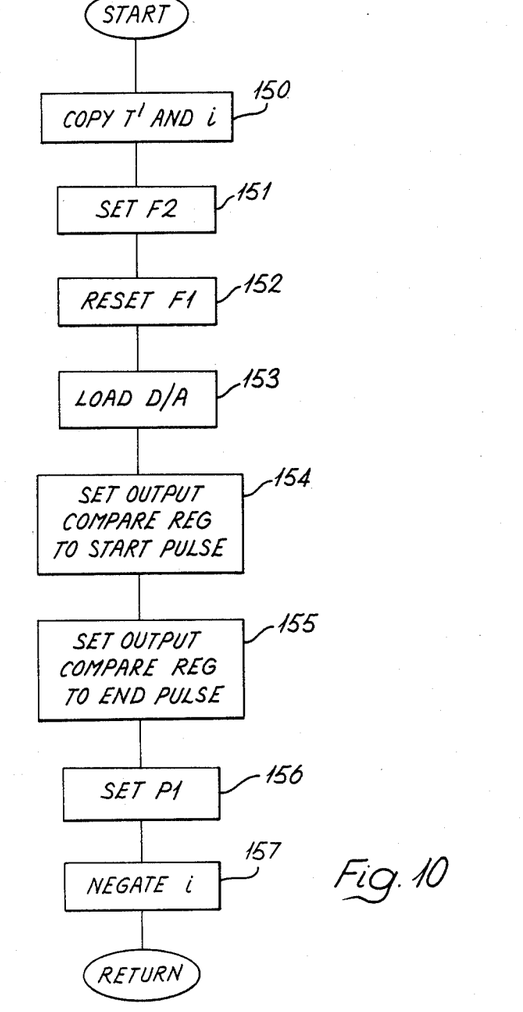

When the "begin output" routine is called the variables T' and i are copied in an operation 150 so that they are available for resetting in the "input capture" routine of FIG. 9. The "output in progress" flag F2 is then set and the "data available" flag F1 is reset in operations 151 and 152. The digital-to-analogue converter 125 is then loaded according to the value i (operation 153) and the output compare register 126 is set to a time, relative to the timer 122, at which a pulse is to start (operation 154). This time is usually set to be as soon as may be convenient after the time t, for example enough time for a few microcomputer operations. When this time is reached, the output compare register 126 gates the digital-to-analogue converter 125 and a positive output pulse commences. After the start of the pulse the contents of the output compare register 126 are again set but to represent a time which is T'/2 after the start of the pulse (operation 155). Operations 156 and 157 are now carried out to set a "phase 1" flag and negate i, respectively, and then a return occurs. When the timer 122 reaches the value held by the register 126 the gating pulse applied by the register to the converter 125 is terminated, the positive half-cycle of the pulse ends and an interrupt is generated.

Figure 11:
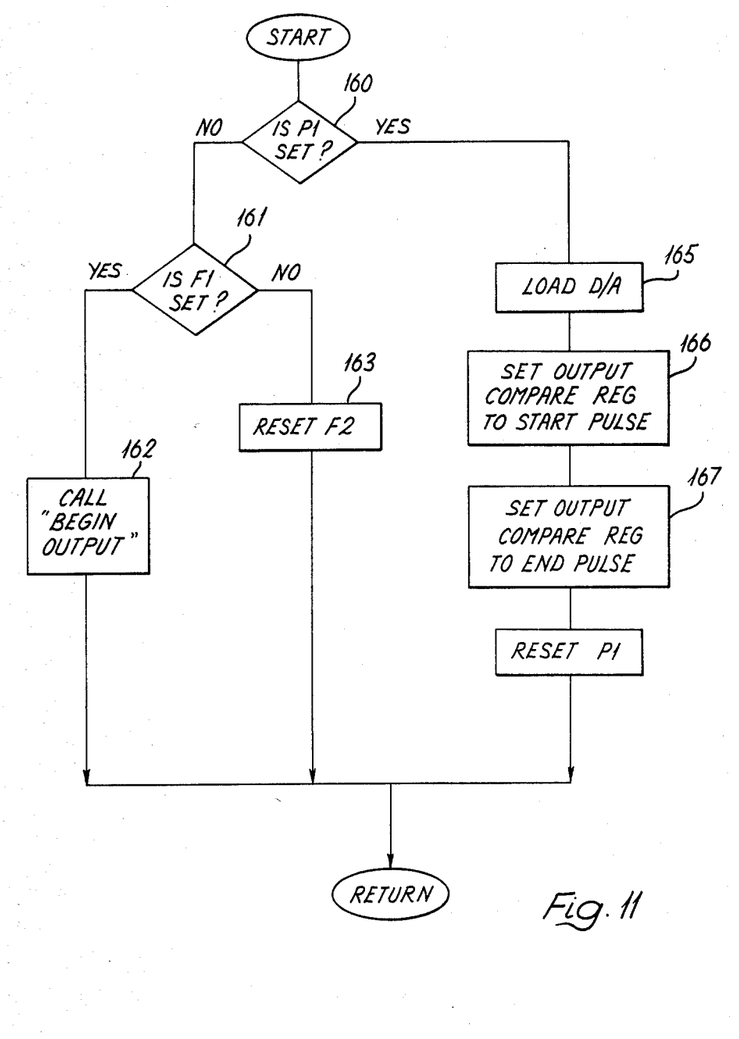

The interrupt calls an "output compare" routine of FIG. 11 which starts with a test 160 to determine whether the "phase 1" flag is set. If not then a further test 161 is carried out to determine whether the data available flag F1 is set. If so then the "begin output" routine of FIG. 10 is called in an operation 162 but otherwise the "output in progress flag" is cleared in an operation 163. Following operations 162 and 163 a return occurs. If the test 160 indicates that the "phase 1" flag is set then the digital-to-analogue converter 25 is loaded with -i (operation 165). The output compare register 126 is then set to initiate a gating pulse for the converter (operation 166). When the terminal 122 reaches the value set in the register 126 a negative output pulse is initiated and then the output compare register is set to a time T'/2 later than the start of the pulse (operation 167). An operation 168 follows in which the "phase 1" flag is reset and then a return occurs. The output pulse ends when the timer 122 reaches the value held by the register 126.

Figure 2D:
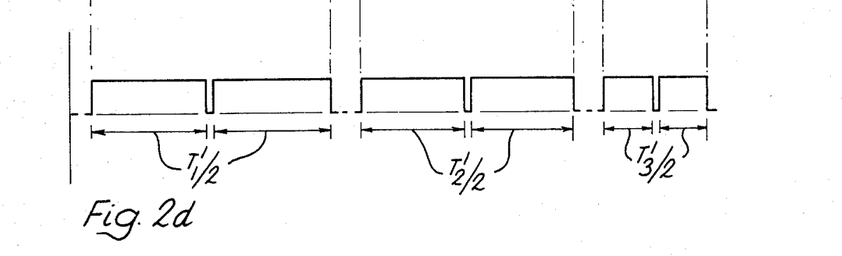

Thus the arrangement of FIG. 8 uses voice period extractor output pulses, for example as shown in FIG. 2b, to generate output pulses from the digital-to-analogue converter 125 which are as shown previously in FIG. 2c, the gating pulses at the output of the output compare register being as shown in FIG. 2d.

Figure 6:
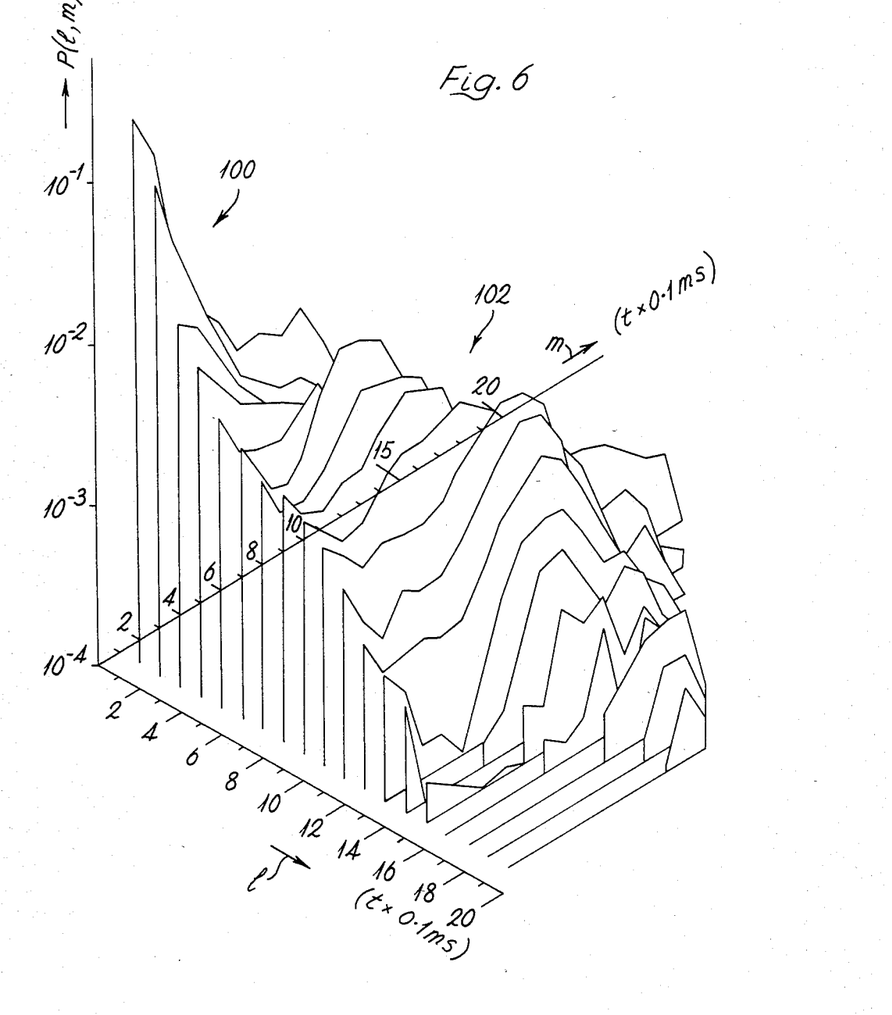
FIG. 6 is a digram probability distribution illustrating the relative frequency of certain combinations of successive intervals between zero crossings occurring in speech.

The device described so far generates a stimulus only when voiced sound occurs but a lip-reading patient can also gain useful information from an indication of the presence of voiceless sounds. The digram distribution of FIG. 6 indicates the probability of first and second intervals having certain respective durations between zero crossings occurring in speech sounds. The speech signal in this particular example has been processed by an amplifier which has a rising 6 db/octave gain characteristic and bandpass filtered between 100 Hz and 5 KHz. The vertical axis indicates probability, the horizontal axis 1 indicates duration of first intervals between zero crossings and the horizontal axis m indicates the duration of second intervals. In the region 100 a short first interval of duration up to 500 microseconds is followed by a short second interval of similar duration and it is this region which corresponds to voiceless sound. The region 102 of first intervals having a duration in the range 1.2 milliseconds to 1.8 milliseconds and a second interval having a duration in the range 0.6 to 1.1 milliseconds is the region where voiced sound occurs. The diagram of FIG. 6 is for male speech but a similar digram distribution can be plotted for female speech.

Figure 7:
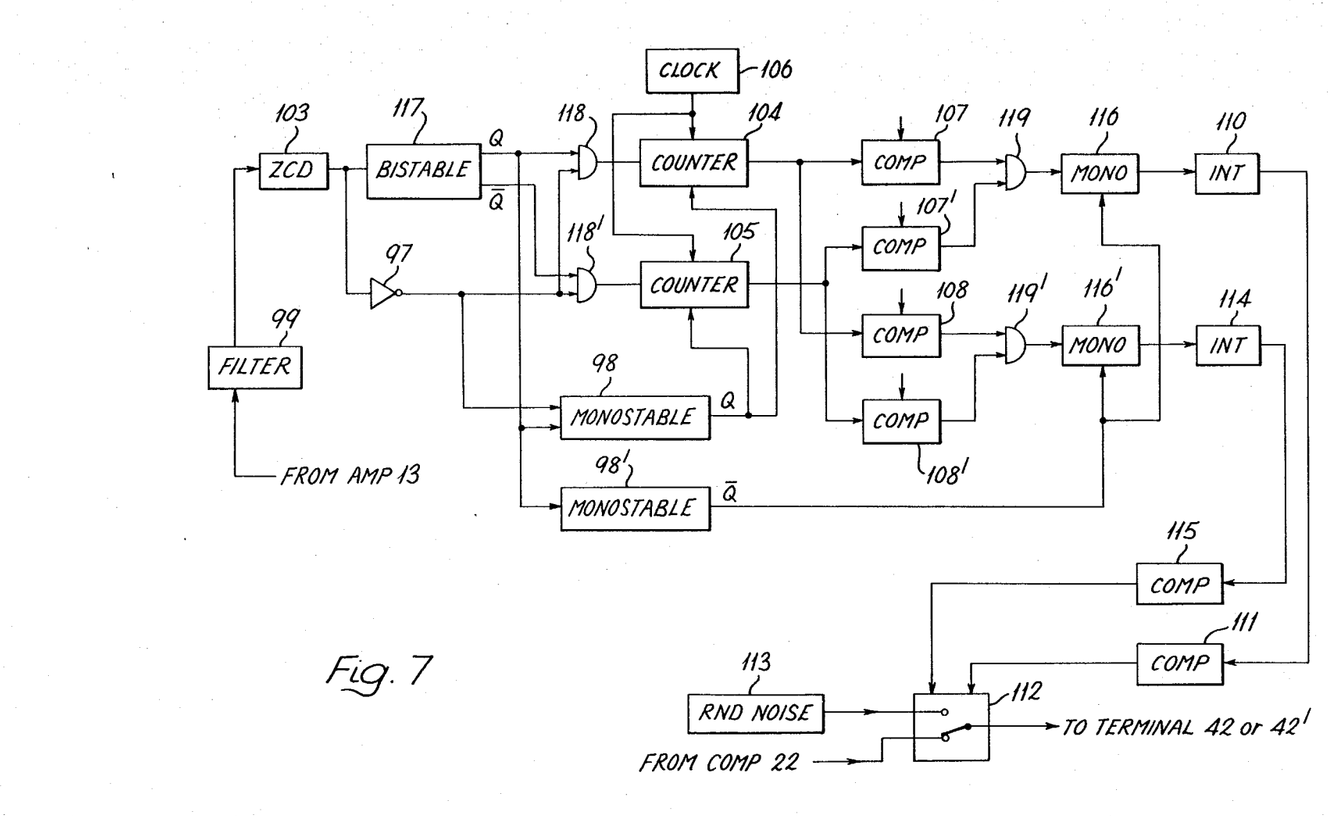
FIG. 7 is a block diagram of means for detecting voiced and voiceless speech.

FIG. 7 shows circuits for distinguishing between voiced and voiceless speech which can be coupled to the circuits of FIG. 4 and FIG. 5 or FIG. 8. The signal from a microphone, amplified using the above mentioned rising gain characteristic, is filtered, for example, from 100 Hz to 5 KHz using a bandpass filter 99 to select an important spectral region for fricatives, and is passed to a zero crossing detector 103 which generates a pulse each time zero crossing occurs. When a first pulse from the detector 103 occurs a bistable circuit 117 is set so that its Q output enables an AND gate 118. After passing through an inverter 97 the trailing edge of the pulse from the detector 103 (now positive going) enables a counter 104 which starts to count pulses from a clock 106. When the next output pulse from the detector 103 is received the $\overline{Q}$ output of the bistable circuit 117 enables an AND gate 118' and the trailing edge of the pulse from the detector 103, after inversion, enables a counter 105. At this time the AND gate 118 is no longer enabled, the counter 104 stops and its contents are proportional to the interval between the first two zero crossings. A monostable circuit 98 is enabled each time the bistable circuit 117 provides a Q output, so that when the detector 103 provides the next output pulse the circuit 98 is enabled. The trailing edge of this pulse after inversion causes the enabled monostable circuit to generate an output pulse whose leading edge resets the counters 104 and 105 and whose duration is short compared with the clock pulse period. Thus the maximum content of the counter 104 represents the interval between a first zero-crossing detector pulse and a second such pulse and the maximum content of the counter 105 represents the interval between the second pulse and a third pulse, these counters being reset only on alternate pulses. The cycle of operation of the counters and their associated circuits is repeated for every pair of detector pulses.

The outputs of the counters 104 and 105 are coupled to magnitude comparators 107, 107', 108 and 108' which may each be of type MC14585. These comparators compare the inputs from the counters 104 and 105 with hard wired inputs indicated by vertical arrows. The comparators 107 and 107' are wired to indicate when a pair of successive intervals is comparatively short, that is the sound received is probably voiceless as indicated in FIG. 6. Thus the hard wired inputs to the comparators 107 and 107' are each equivalent to, for example, 0.5 mS (that is the signal applied to these comparators is equivalent to the number of pulses received from the clock 106 in 0.5 mS). The comparators 107, 107', 108 and 108' have three outputs which correspond to the three conditions: one input equal to the other input; one input greater than the other input; and the said one input less than the said other input. Those outputs from the comparators 107 and 107' which indicate that the inputs from the counters 104 and 105 are less than the hard wired inputs are connected to an AND gate 119 so that provided that the interval measured by the counters 104 and 105 does no exceed 0.5 mS the AND gate 119 is opened and a monostable circuit 116 is enabled. Alternate pulses from the detector 103 as derived at the Q output of the bistable circuit 117 trigger a monostable circuit 98' to trigger the monostable circuit 116, if enabled, some time after the leading edge of the detector pulse but before the trailing edge of the said pulse. The monostable circuit 116 then passes a pulse to an integrator circuit 110. The comparator 108 has a hard wired input corresponding to 1.2 mS and that one of its outputs which corresponds to the input from the counter 104 being greater than the hard wired input is coupled to an AND gate 119'. The hard wired input to the comparator 108' is set to correspond to 0.6 mS and that one of its outputs which corresponds to the input from the counter 105 being greater than the hard wired input is connected to the AND gate 119'. In this way a monostable circuit 116' is only enabled if the first interval in a pair of intervals between detector pulses is greater than 1.2 mS and the second pulse is greater than 0.6 mS, that is as indicated by FIG. 6 the sound received is likely to be voiced. Each time this condition occurs an integrator 114 receives an input pulse when the monostable circuit 116 is triggered by the trailing edge of a pulse from the monostable circuit 98'.

Should the integrator 110 receive enough pulses in an interval which is short compared with its time constant, a predetermined threshold of a comparator 111 is exceeded and a solid state switch 112 operates connecting a random noise generator 113 to the terminal 42 of FIGS. 4 and 5 or the terminal 42' of FIG. 8. At the same time the output from the comparator 22 of FIG. 1 is disconnected. The patient then receives a stimulus related to random noise and indicative of voiceless sound. The time constant of the integrator 110 is about 2 mS. If first and second intervals between detector pulses in a pair of such intervals are greater than 1.2 and 0.6 mS, respectively, the integrator 114 receives an input pulse and if, within a time which is short in comparison with a time constant of this integrator, enough such pulses are received to exceed a predetermined threshold of a comparator 115 it is an indication that the input is voiced. The switch 112 then takes up that state in which the comparator 22 of FIG. 1 is connected to terminal 42 of FIGS. 4 and 5 or 42' of FIG. 8. The patient then receives a stimulus indicative of the frequency of a voiced sound. The time constant of the integrator 114 is about 10 mS. If neither of the comparators 111 or 115 exceed their respective thresholds the switch 112 is biassed to that state in which the comparator 22 is connected to the terminal 42. Clearly a logic circuit to replace that of FIG. 7 can be devised to perform an algorithm which more definitely delineates the regions 100 and 102 in FIG. 6. For example rectangular boundaries can be given to these regions and pulses only sent to the integrators 110 and 114 when the comparators 107 and 108 indicate the occurrence of points within the respective rectangular boundaries.

A logic circuit or computer algorithm giving such boundaries employs the following limits: $L_0=0.5$ mS, $L_1=1.2$ mS and $L_2=1.8$ mS along the 1 axis and $M_0=0.5$ mS, $M_1=0.6$ mS and $M_2=1.1$ mS along the m axis of FIG. 6.

If $L_1<1<L_2$ and $M_1<m<M_2$ and speech is present then the sounds are voiced. If $1<L_0$ and $m<M_0$ and speech is present the sounds are voiceless. The presence of speech can be determined using a detector which signals when the mean of the input signal exceeds a predetermined threshold.

While certain embodiments of the invention have been described it will be realised that the invention can be put into practice in many other ways. For example the circuit of FIG. 5 can be replaced by any circuit which ensures that the capacitor isolating a patient transmits no net charge in an interval of not more than three voice periods. FIG. 7 may be replaced by other logic or analogue circuits for distinguishing between voiced and voiceless sounds on the basis of the digram distribution of FIG. 6. Similarly the filtering applied to the input speech in FIG. 7 may be changed dependent on ambient noise and other processing conditions. For example a bandpass filter, having a pass band from 1 KHz to 6 KHz may be used if it is desired to discriminate against low frequency noise, the digram boundaries being correspondingly changed. Where analogue circuits are used the counters 104 and 105 may be replaced by integrators which integrate for periods between zero crossings. Analogue comparisons of the outputs of these integrators can be made to control further analogue integrators and comparators controlling the switch 112.

The characteristics of the output of the generator 113 may be controllable in response to different fricative sounds in order to indicate such sounds to a patient.

Much of FIGS. 1, 3 to 5 and 7 may be replaced by a microprocessor and associated circuits programmed to carry out functions equivalent to the blocks shown.

Some of the circuits shown may be implanted in the patients body, for example the output of the potentiometer 90 in FIG. 5 may be coupled to an electromagnetic or acoustic transmitter when a receiver is implanted together with the components shown to the right of the potentiometer 90 (or components having similar functions).

The invention can be used in many other applications where electrical stimulation of the human or animal body is required.

We claim:

1. Apparatus for the electrical stimulation of nerves comprising
    stimulus means for generating an electrical stimulus of alternating polarity and varying periods, which is non-zero for most of the duration of most of the said periods,
    an electrode for location in a position where a nerve can be stimulated, and
    charge control means for ensuring that the net charge applied to the electrode is zero in each of successive intervals substantially throughout stimulation, each interval having a duration equal to an integral number of said periods not greater than three.

2. Apparatus according to claim 1 including a capacitor coupled between the stimulus means and the electrode, the charge control means, in operation, ensuring that the net charge applied to the capacitor is zero in each of said successive intervals.

3. Apparatus for aiding the deaf according to claim 1 including
    means for determining the voice period of voiced sounds which are to be used in providing the said electrical stimulus,
    wherein the stimulus means are constructed to generate one alternating current cycle per voice period, the net charge applied by the charge control means to the electrode being zero in each voice period.

4. Apparatus according to claim 3 including means which allow the generation of one cycle of the stimulus only each time one complete voice period has been detected thus ensuring that when voice periods are no longer detected stimulation ceases.

5. Apparatus according to claim 3 for use when the cochlea is stimulated, including means for so reducing the frequency of the stimulus from the frequency which corresponds to voice period that substantially the whole range of resulting stimulation periods falls within the range of stimulus periods to which the normal cochlea is sensitive.

6. Apparatus according to claim 1 including means for increasing the amplitude of stimulation with increase in frequency thereof.

7. Apparatus for aiding the deaf according to claim 1 including means for providing a distinctive stimulus when voiceless sounds occur.

8. Apparatus according to claim 7 wherein the means for providing a distinctive stimulus comprises
    means suitable for coupling to a sound transducer for determining respective intervals between signal reversals in the transducer output signal,
    means for indicating the presence of voiceless sounds when, in each of a group of pairs of successive said intervals, the durations of the intervals are both shorter than a predetermined interval, and
    means for indicating the presence of voiced sounds when, in each of a group of pairs of successive said intervals, the duration of the first interval is in a first predetermined range and the duration of the second interval is in a second predetermined range.

9. Apparatus for determining the voice period of voiced sounds comprising
    a transducer for providing an electrical signal representative of sounds,
    a logarithmic amplifier coupled to the transducer by way of a low-pass filter, and
    peak detection means coupled to the amplifier output and arranged to respond to the first peak in each voice period of the sound representative signal to generate an output pulse each time the said signal indicates that the vocal cords of a speaker making the voiced sounds have closed.

10. Apparatus according to claim 3 wherein the means for determining the voice period of voiced sounds comprises
    a transducer for providing an electrical signal representative of sounds,
    a logarithmic amplifier coupled to the transducer by way of a low-pass filter, and
    peak detection means coupled to the amplifier output and arranged to respond to the first peak in each voice period of the sound representative signal to generate an output pulse each time the said signal indicates that the vocal cords of a speaker making the voiced sounds have closed.

11. Apparatus according to claim 9 wherein the peak detection means comprises
    first and second peak detection circuits coupled by a signal differentiation circuit.

12. Apparatus according to claim 9 wherein the transducer is a microphone which in operation does not introduce a relative phase delay between the fundamental component and its second harmonic greater than one twentieth of the fundamental period.

13. Apparatus according to claim 9 including means for discarding the output pulses from the peak detection means unless a preceding pulse occurred within an interval which is not longer than the longest expected pitch period.

14. Apparatus for distinguishing between voiced and voiceless speech sounds comprising
    means suitable for coupling to a sound transducer for determining respective intervals between signal reversals in the transducer output signal, and
    means for indicating the presence of voiceless sounds when, in each of a group of pairs of successive said intervals, the durations of the intervals are both shorter than a predetermined interval.

15. Apparatus according to claim 14 including a bandpass filter having a pass band of from 100 Hz to 5 KHz for input signals and means for amplifying the filter output signals using a characteristic which rises at 6 db per octave to provide input signals for the means for determining respective intervals, wherein the predetermined interval is 500 microseconds.

16. Apparatus according to claim 15 including
means for indicating the presence of voiced sounds when, in each of a group of pairs of successive said intervals, the duration of the first interval is in the range 1.2 to 1.8 milliseconds and the duration of the second interval is in the range 0.6 to 1.1 milliseconds.

17. Apparatus according to claim 14 including
means for indicating the presence of voiced sounds when, in each of a group of pairs of successive said intervals, the duration of the first interval is in a first predetermined range and the duration of the second interval is in a second predetermined range.

* * * * *